(12) United States Patent
Waldron et al.

(10) Patent No.: US 8,221,437 B2
(45) Date of Patent: Jul. 17, 2012

(54) DEVICE FOR APPLYING LIQUID SKINCARE PRODUCTS IN COMBINATION WITH VACUUM AND ABRASION

(75) Inventors: Stephen H. Waldron, Camarillo, CA (US); Paula Kent, Ventura, CA (US)

(73) Assignee: Altair Instruments, Inc., Camarillo, CA (US)

( * ) Notice: Subject to any disclaimer, the term of this patent is extended or adjusted under 35 U.S.C. 154(b) by 21 days.

(21) Appl. No.: 12/953,979

(22) Filed: Nov. 24, 2010

(65) Prior Publication Data

US 2011/0295273 A1 Dec. 1, 2011

Related U.S. Application Data

(60) Provisional application No. 61/264,526, filed on Nov. 25, 2009.

(51) Int. Cl.
*A61B 17/50* (2006.01)
(52) U.S. Cl. ...................................................... 606/131
(58) Field of Classification Search .................. 606/131, 606/132, 133; 132/73.6, 76.4; 604/289, 604/290, 318–327, 45, 119, 266, 267
See application file for complete search history.

(56) References Cited

U.S. PATENT DOCUMENTS

| | | | |
|---|---|---|---|
| 2,631,583 A * | 3/1953 | Lavergne | 601/7 |
| 6,241,739 B1 | 6/2001 | Waldron | |
| 6,500,183 B1 | 12/2002 | Waldron | |
| 6,527,783 B1 | 3/2003 | Ignon | |
| 6,592,595 B1 | 7/2003 | Ignon | |
| 6,629,983 B1 | 10/2003 | Ignon | |
| 6,695,853 B2 | 2/2004 | Karasiuk | |
| 6,942,649 B2 | 9/2005 | Ignon | |
| 2008/0215068 A1* | 9/2008 | Hart et al. | 606/131 |
| 2009/0062815 A1 | 3/2009 | Karasiuk | |
| 2009/0177171 A1 | 7/2009 | Ignon | |
| 2009/0222023 A1 | 9/2009 | Karasiuk | |

* cited by examiner

*Primary Examiner* — Tuan V Nguyen
(74) *Attorney, Agent, or Firm* — Koppel Patrick Heybl & Philpott; Michael J. Ram

(57) ABSTRACT

A liquid delivery wand includes a centrally located fluid storage chamber. An absorbent pad is located within the working end of the wand for applying the treatment liquid to the skin while a vacuum is applied to the skin through an abrasive coated treatment tip. Coaxial, cylindrical tubes with flow channels between tube surfaces control the flow rate, the pressure drop being established by the close fit and length of adjacent surfaces of the coaxial components. The flow rate of the liquid is adjustable by simply rotating the interfitting components. The chamber that holds the liquid is sealed from the atmosphere at the distal and proximal end. When the wand is connected to vacuum and the distal end contacts the skin, the vacuum applies a negative pressure to the fluids within a fluid chamber. A small portion of liquid is thus transferred to wet the filter pad.

4 Claims, 8 Drawing Sheets

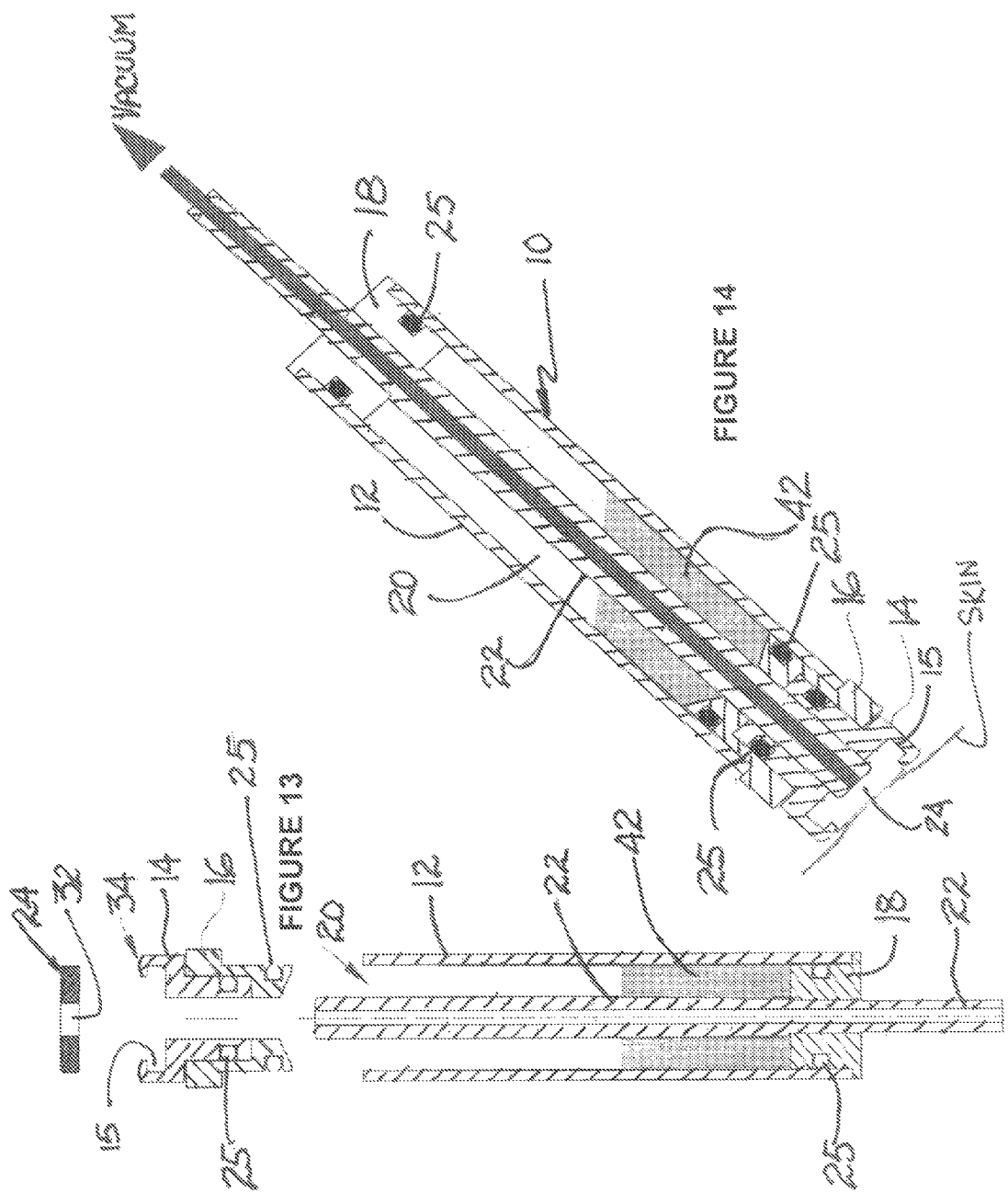

DEVICE FOR APPLYING LIQUID SKINCARE PRODUCTS IN COMBINATION WITH VACUUM AND ABRASION

This application claims benefit of U.S. Provisional Application 61/264,526 filed Nov. 25, 2009.

Disclosed herein is a device and system for providing a skin treatment utilizing a skin enhancing fluid delivery system to provide both skin exfoliation using an abrasive coated working surface and skin hydration during one treatment.

BACKGROUND

Waldron U.S. Pat. No. 6,241,739, incorporated herein in its entirety by reference herein, shows the basic concept of a micro-dermabrasion system using an abrasive surface and vacuum to remove the outer layer of skin. FIG. 11 of the patent shows a method of connecting a fluid source to the microdermabrasion instruments.

U.S. Pat. No. 6,500,183 (Waldron) describes a device using a rotating abrasive disc, vacuum and irrigation fluid to abrade the skin during the procedure. However, that patent does not show capturing the irrigation fluids. This design is intended for aggressive dermabrasion of patients with burns or scars where the fluids are intended to remove dead skin and other debris.

US Published Patent Application 2009/0222023 (Karasiuk) describes a micro-dermabrasion device where the fluids are stored in a secondary bottle and delivered to the hand piece through a tube. This type of product delivery inherently wastes the product in the tubing and is difficult to clean after the treatment.

US Published Patent Application 2009/0062815 (Karasiuk) describes a hand held instrument for micro-dermabrasion where the abrasive surfaces wiggle back and forth and skincare product is ejected onto the skin from a chamber and through tubing. The force to eject the fluid is a spring-actuated plunger.

U.S. Pat. No. 6,695,853 (Karasiuk) describes a micro-dermabrasion device where fluids are delivered to the skin via a tube from a remote container. The vacuum which contacts the skin is exterior to the abrasive surface.

US Published Patent Application 2009/0177171 (Ignon) describes a micro-dermabrasion device that uses a secondary storage container for the skincare products which is delivered to the instrument through a secondary tube.

U.S. Pat. No. 6,942,649 (Ignon) describes an instrument to apply dry material in coordination with an abrasive surface and vacuum. The abrasive surface is in the center of the instrument and the vacuum is on the periphery of the abrasive surface.

U.S. Pat. No. 6,527,783 (Ignon) and U.S. Pat. No. 6,592,595 (Ignon) use aluminum oxide as an abrasive material.

U.S. Pat. No. 6,629,983 (Ignon) uses abrasive pads. There is no mention of skincare product application.

BRIEF DESCRIPTION OF THE DRAWINGS

FIG. 4 is a cross section through the wand tip taken along line 4-4 of FIG. 6 and FIG. 5 is a cross section through the front seal taken along line 5-5 of FIG. 6.

FIGS. 7-9 are cross section views of the liquid applicator showing an intermediate flow arrangement. FIG. 9 is a longitudinal cross section of the liquid applicator. FIG. 7 is a cross section through the wand tip taken along line 7-7 of FIG. 9 and FIG. 6 is a cross section through the front seal taken along line 8-8 of FIG. 9.

FIG. 12 is a longitudinal cross section of the liquid applicator. FIG. 10 is a cross section through the wand tip taken along line 10-10 of FIG. 12 and FIG. 11 is a cross section through the front seal taken along line 11-11 of FIG. 12.

FIG. 13 is a partially expanded longitudinal cross sectional view of the applicator of FIG. 2 partially filled with fluid.

FIG. 14 is an assembled longitudinal cross sectional view of the applicator of FIG. 2 applied to a skin surface while a vacuum is also applied to the skin surface.

SUMMARY

Skin care products and serums are expensive and must be applied with minimum waste. They also must be applied uniformly. To do so, a liquid delivery wand includes a centrally located fluid storage chamber and an absorbent pad located within the working end of the wand for applying the treatment liquid to the skin while a vacuum is applied to the skin through the application tip. The skin is stretched partially into the center chamber and contacts the pad containing the liquid treatment. Only very small amounts of skincare product are lost to the vacuum system as a result of this arrangement.

The entire wand can be disassembled for cleaning and sterilization after treatments. There are no small orifices such as needle valves to control fluid flow rates. Coaxial, cylindrical tubes with flow channels between tube surfaces control the flow rate, the pressure drop being established by the close fit and length of adjacent surfaces of the coaxial components. The components are configured to have an adjustable flow rate of the liquid by simply rotating the interfitting components. To conserve expensive skincare products the chamber that holds the liquid is sealed from the atmosphere at the distal end. When the wand is connected to vacuum and the distal end contacts the skin, the vacuum applies a negative pressure to the fluids within a fluid chamber. A small portion of liquid is thus transferred to wet the filter pad. When the pressure (vacuum) equalizes, which occurs quickly, the liquid stops flowing. Minimal or no treatment fluid is lost to the vacuum tube, as air instead of liquid is sucked in to the vacuum line when the device is partially occluded or lifted from the skin. Flow from the storage chamber through into the pad can only occur when the tip of the delivery wand is fully occlude by the skin surface, said flow ceasing as soon as the pressures are equalized creating a sealed chamber.

The use of the instrument shortens the time of the treatment by doing both the dermabrasion and applying the treatment solution at the same time. The use of vacuum to apply the solution insures a deeper penetration of the solutions into the tissue. Common skincare products for use in the device are vitamins, hydrating solutions or serums.

DETAILED DESCRIPTION

Figure 1:
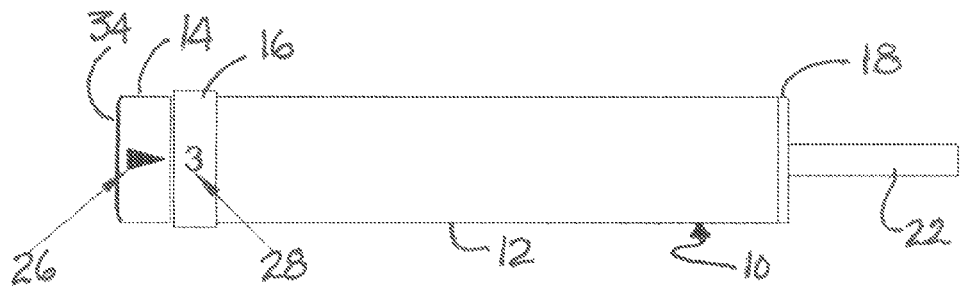
FIG. 1 is a side view of a liquid applicator incorporating features of the invention.
Figure 2:
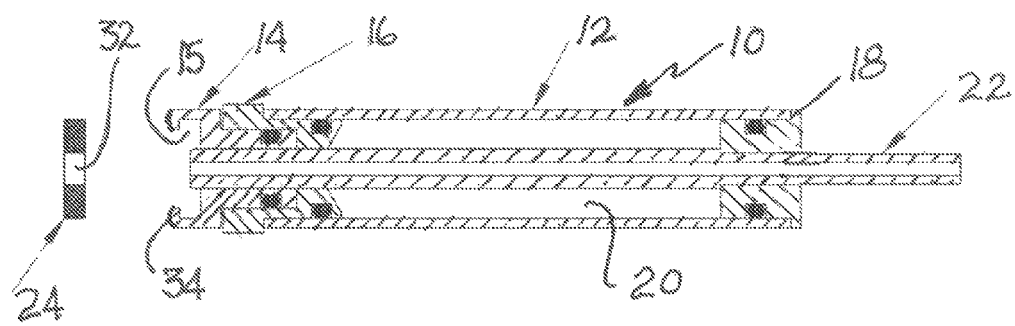
FIG. 2 is a longitudinal cross section view of the liquid applicator of claim one, including a skin contacting pad prior to attachment to the applicator.
Figure 3:
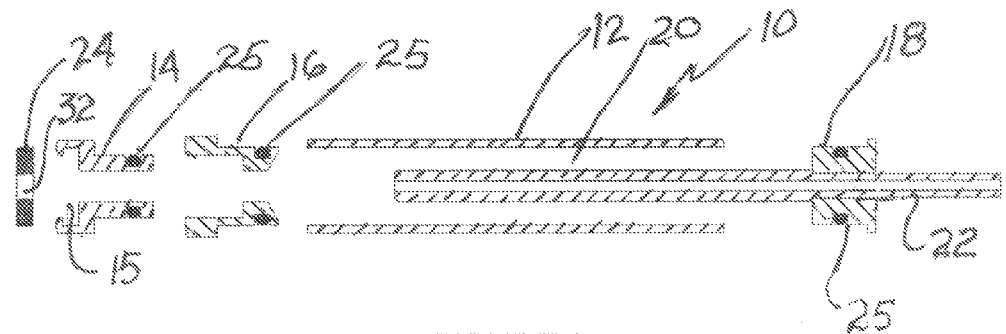
FIG. 3 is an expanded view of the applicator of FIGS. 1 and 2.
Figure 4:
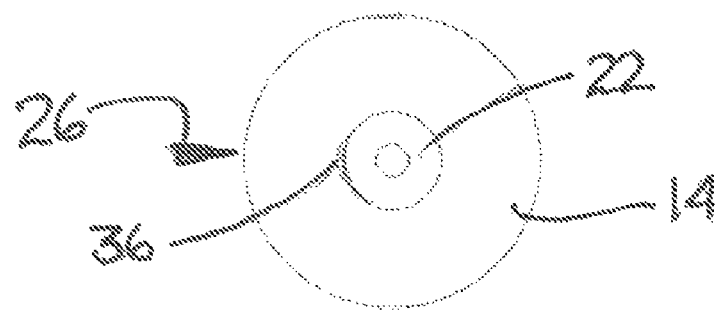
FIGS. 4-6 are cross section views of the liquid applicator showing the highest flow arrangement.
Figure 5:
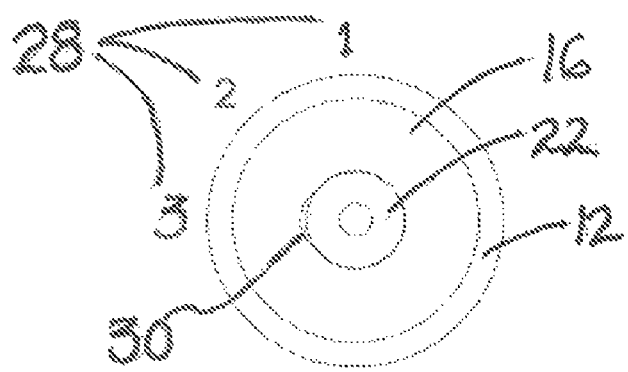
Figure 6:
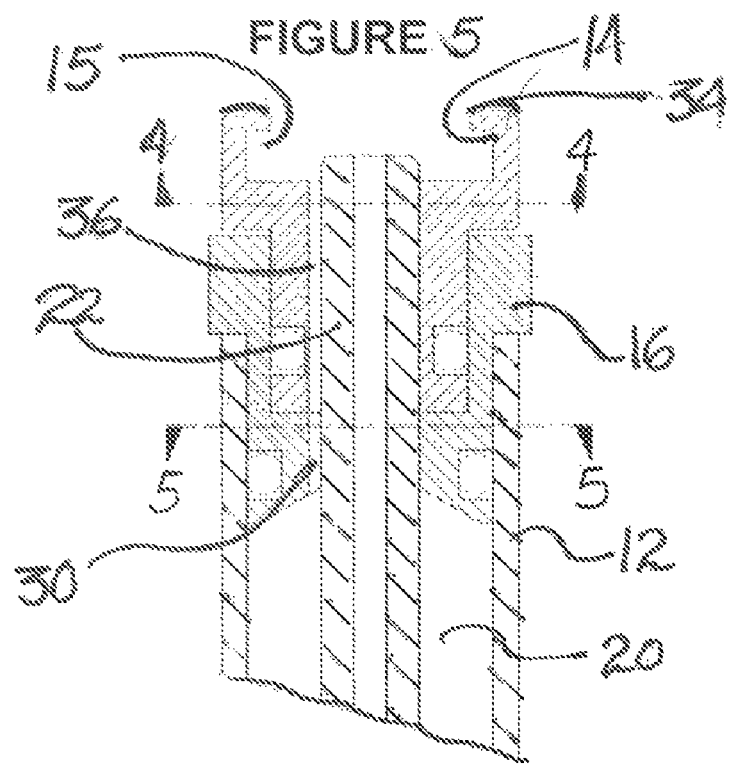

Referring to FIGS. 1-3, a device incorporating features of the invention is shown. FIG. 1 is a side view showing the liquid delivery wand 10. FIG. 2 is a cross sectional view of the wand 10 of FIG. 1 and FIG. 3 is an exploded cross-sectional view of the wand 10. The wand 10 comprises a tubular cylinder 12 having, a front seal 16, a wand tip 14 rotationally mounted within the front seal 16 and a rear seal 18 on the opposite end of the cylinder 12 to form an enclosed space 20 between the front and rear seals 16,18. The distal surface of the wand tip has an abrasive surface 34, preferably formed by diamond crystals permanently bonded thereto such as shown in applicant's prior U.S. Pat. Nos. 6,241,739 and 6,500,135, said patents incorporated herein, in their entirety, by reference. Alternatively, the wand tip can be coated with other abrasive substances or left uncoated A vacuum tube 22 has a distal end within a hole longitudinally through the center of the wand tip 14 and into a pad chamber 15 in the wand tip 14 and extends distally into the pad chamber 15 through the front seal 16, the enclosed space 20, and through the rear seal 18 with a proximal end extending outward for attachment to a vacuum source (not shown). The outer diameter of the vacuum tube at the point where it passes through the front seal and the wand tip is just slightly smaller than the inner diameter of those two components so that flow of fluid held within the enclosed space 20 is substantially restricted but for the grooves 30, 36 and 40. A filter pad 24 is located within the wand tip 14. Preferably the filter pad 24 has a central hole 32 which coincides with the distal end of the vacuum tube 22. In use, the fluid in the delivery wand 10 passes into the pad chamber 15, the pad 24 and onto the skin surface being treated. Each of the front seal 16, rear seal 18 and wand tip 14 have O-ring seals 25, or similar sealing devices, to form a liquid tight seal with the component which is around it. For example, an O-ring seal 25 is located between the front seal 16 and the rear seal 18 in the first instance and the cylinder 12 as well as between the wand tip 14 and the front seal 16 as best shown in FIG. 2. The cylinder 12, wand tip 14, front seal 16 and rear seal 18 are reusable while the filter pad 24 is a single use disposable. The parts can be disassembled for cleaning between treatments as shown in FIG. 3.

FIG. 1 shows markings to indicate the flow rate comprising an indicator arrow 26 on the outer surface of the wand tip 14 and indicia 28 indicating flow settings on the outer surface of the front seal, as explained below. One of the three flow settings (1, 2 and 3 with only 3 being shown) is shown marked on the outer surface of the front seal 18. The indicia on the front seal aligns with a longitudinal groove 30 on the inner surface of the front seal 18, as shown in FIGS. 5, 6, 8, 9, 11 and 12. The indicator arrow 26 aligns with a longitudinal groove 36 on the inner surface of the wand tip 14, as best shown in FIGS. 4, 6, 7, 9 and 10. The wand tip 14 can be rotated in relationship to the front seal 16 to control the fluid flow rate as explained below. While the indicator arrow 26 and the indicia 28 are marked on the surface of the tip 14 and front seal 16 respectively, for clarity in explaining fluid flow with reference to FIGS. 4-12 their locations are shown in said Figures next to the components instead of on the adjacent surface thereof.

Referring to FIGS. 4-12, flow rate of the fluid from the enclosed space 20 through the wand tip 14 of the liquid delivery wand 10 is adjusted by applying a vacuum to the lumen of the vacuum tube 22 and rotating the wand tip 14 within the front seal 16. Flow is maximized when the arrow 26 on the wand tip 14 is positioned pointing to the number 3 (indicia 28) on the front tip 16 as shown in FIG. 1 and FIGS. 4-6. When so positioned the groove 30 on the inner surface of the front seal 16 aligns with the tip seal groove 36 on the inner surface of the wand tip 14, the fluid flowing through the aligned grooves 30, 36. This provides the maximum area for fluid flow. The cross sectional area of the groove available for fluid flow in a preferred embodiment is 0.0024 in$^2$ (1.5 mm$^2$).

Figure 7:
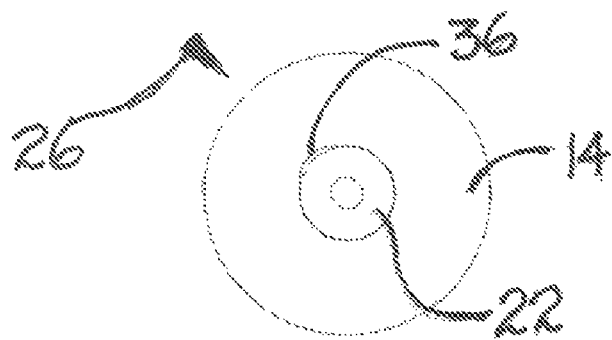
FIG. 7 is a longitudinal cross section of the liquid applicator.
Figure 8:
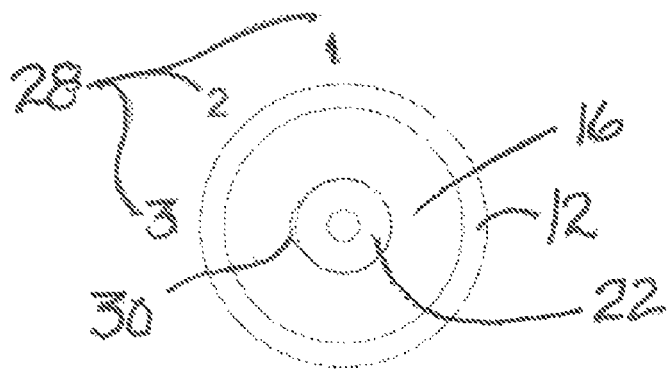
Figure 9:
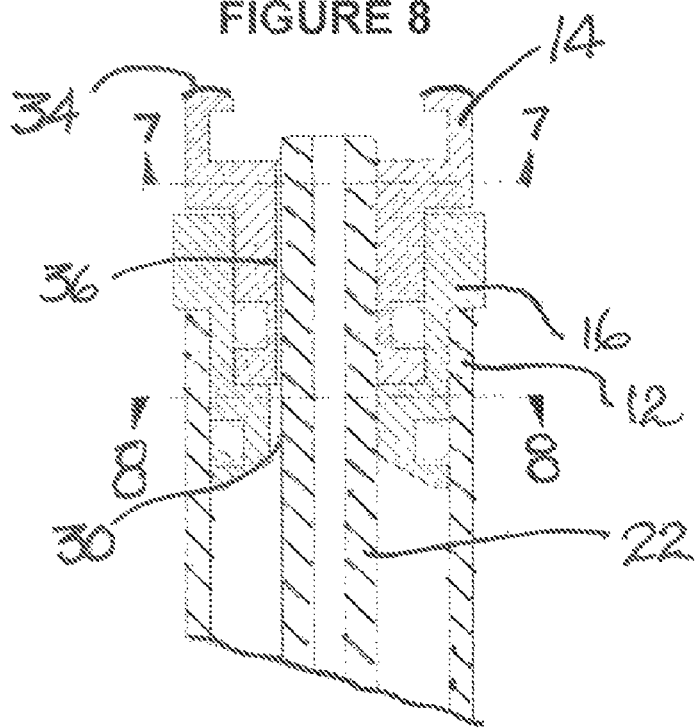

Flow is reduced to an intermediate rate when the arrow 26 on the wand tip 14 is positioned pointing to the number 2 (indicia 28) on the front tip 16. As shown in FIGS. 7-9, when so positioned the groove 30 on the inner surface of the front seal 16 only partially aligns with the tip seal groove 36 on the inner surface of the wand tip 14, the fluid flowing through the partially aligned grooves 30, 36 being partially restricted by the reduced alignment. With the wand tip rotated 45 degrees from the maximum position, as shown in FIG. 7, towards the number 2 the area open for fluid flow is 0.0011 in$^2$ (0.7 mm$^2$). Of course various orientations other than 45 degrees from the maximum position can be used to provide various intermediate flow rates.

Figure 10:
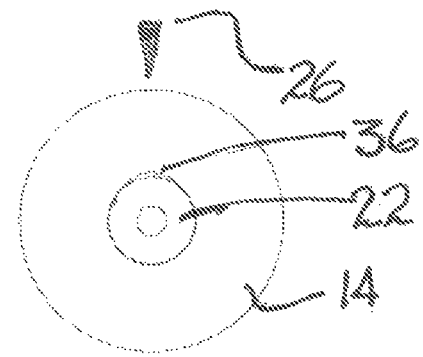
FIGS. 10-12 are cross section views of the liquid applicator showing the lowest flow arrangement.
Figure 11:
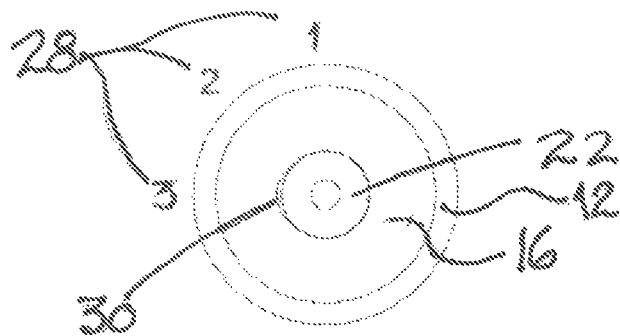
Figure 12:
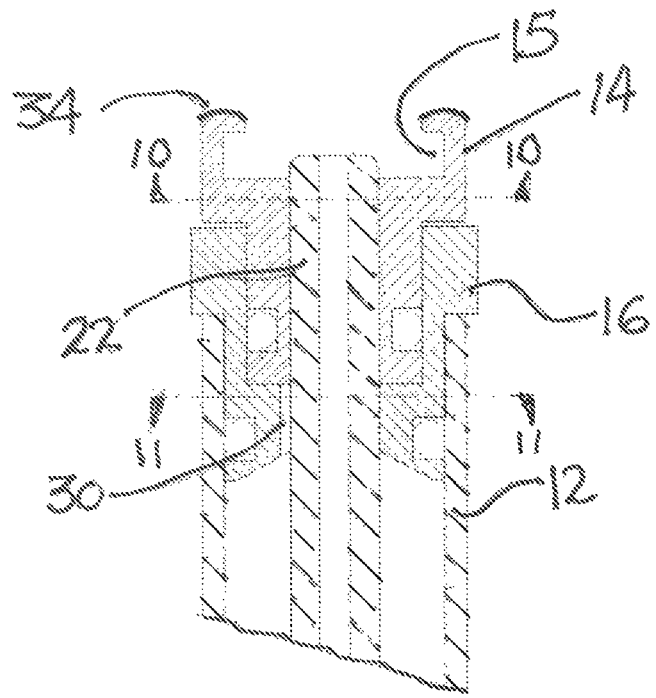
Figure 16:
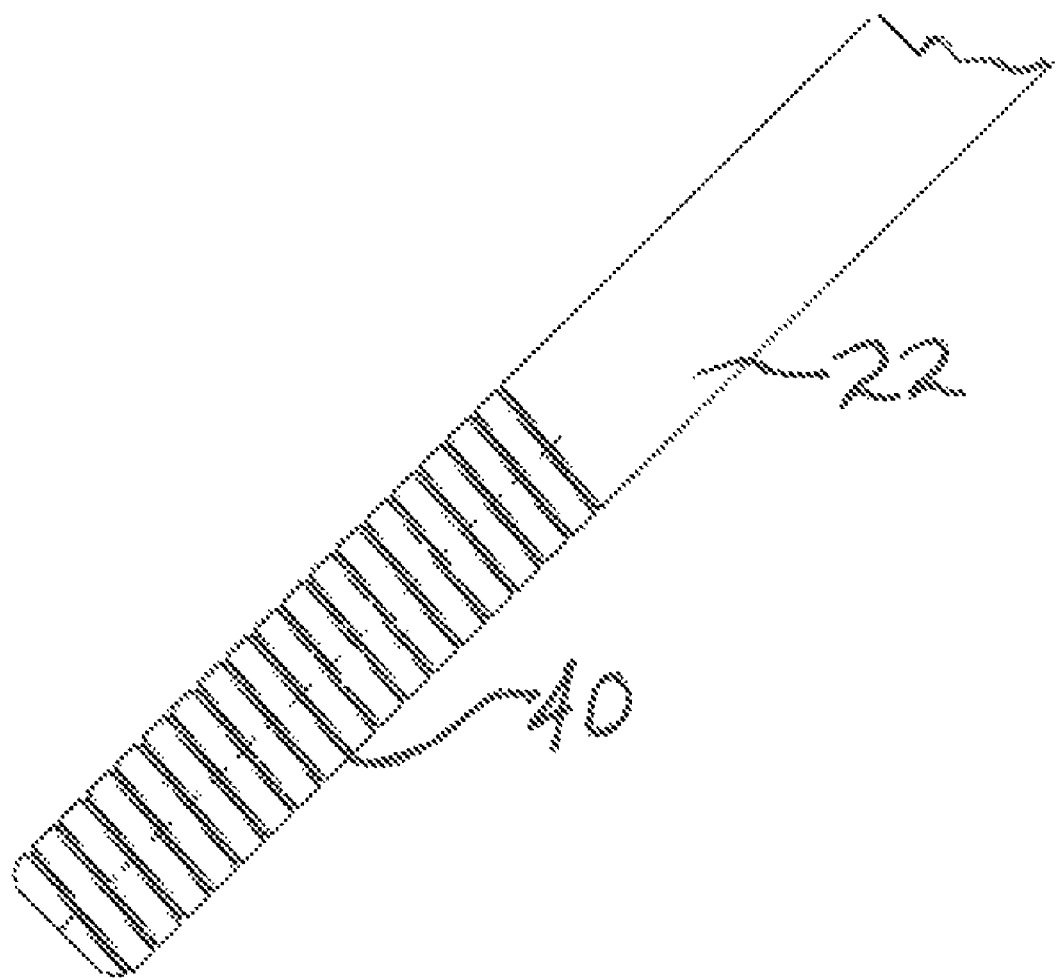
FIG. 16 is view of the exterior surface of the distal portion of the vacuum tube.

Flow is reduced to its lowest rate when the arrow 26 on the wand tip 14 is positioned pointing to the number 1 (indicia 28) on the wand tip 16. The wand tip 16, as shown in FIG. 10, is rotated 90 degrees from the maximum position for minimum flow. As shown in FIGS. 10-12, when so positioned the groove 30 on the inner surface of the front seal 16 does not align with the tip seal groove 36 on the inner surface of the wand tip 14. However, as shown in FIG. 16, the outer wall of the vacuum tube 22 has a spiral groove 40, with a depth of about 0.020 inches, along its outer surface. In this instance the flow is predominantly through the groove 40 on the vacuum tube 22 outer surface that is located adjacent the inner surfaces of the front seal 16 and the wand tip 14. In this case the area open for fluid flow is 0.0008 in$^2$ (0.5 mm$^2$).

Figure 15:
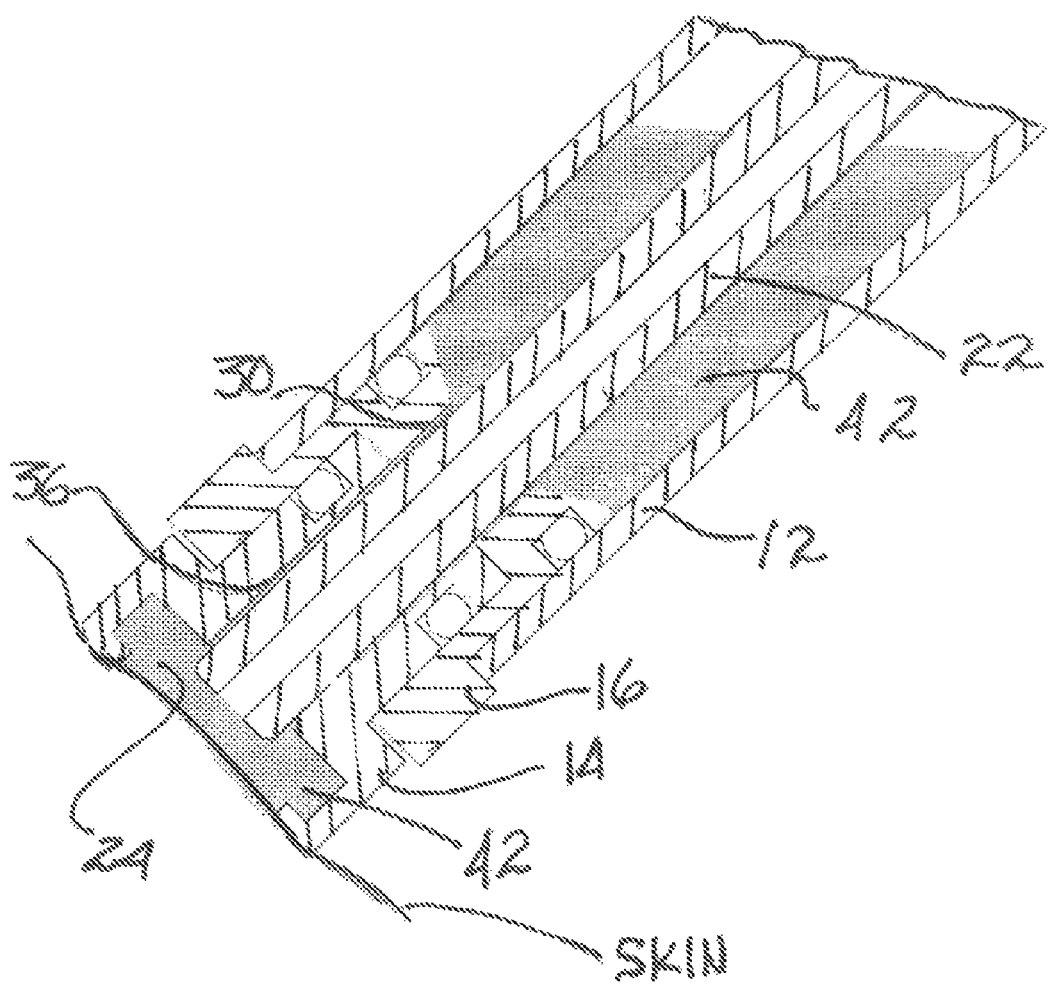
FIG. 15 is an assembled longitudinal cross sectional view of the applicator of FIG. 2 applied to a skin surface during fluid deliver.

FIG. 15 shows the fluid path from the enclosed space 20, along the aligned grooves 30, 36 in the maximum flow orientation and into the filter pad 24. Even though a vacuum is applied to the vacuum tube 22, the fluid is not drawn up the vacuum tube 22 because the end is sealed against the skin and no air can flow through the tube. When the handpiece is removed from the skin, such as shown in FIG. 14, air flows passed the tip and through the vacuum tube but the majority of fluid is still captured in the filter pad and remains in the enclosed space 20 because no vacuum is applied to the fluid therein.

Vacuum pressure also affects the flow rate of the fluid. A reasonable setting for fluids with the viscosity similar to water is minimum flow (a setting of "1" on the wand tip) and 8 in-hg negative pressure. For viscous fluids a setting of "3" and a vacuum of 10 in-hg gives a proper flow. However, one skilled in the art will recognize that the 0°, 45° and 90° orientation of the indicator arrow 26 are only suggested settings and any orientation within that range, or greater than 90°, can be used. However, further rotation will not further reduce flow.

Figure 17:
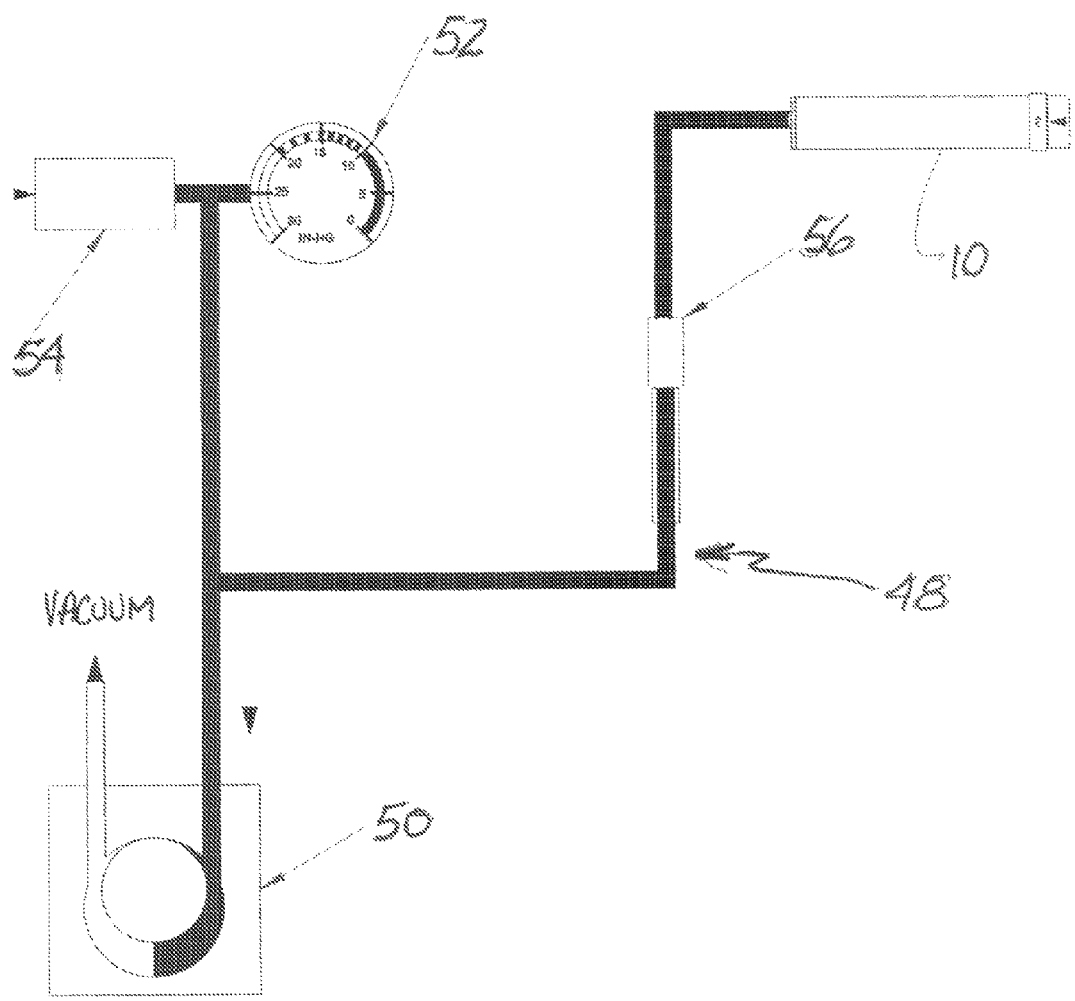
FIG. 17 is a schematic diagram of a fluid delivery and skin treatment system incorporating the fluid applicator of FIGS. 1-11.

FIG. 17 shows the schematic of a vacuum system 48 incorporating the liquid delivery wand 10. The vacuum pump 50 typically has a variable output from zero to 25 in-hg. Setting between 5 to 12 in-hg are preferred. The vacuum pressure gauge 52 is included to monitor the vacuum pressure which is adjusted by the metering valve 54. A filter 56 is included to remove debris from the vacuum air stream.

To use the device described above the liquid delivery wand 10 is opened by removing the wand tip 14 and front seal 16 as shown in FIG. 13 and the treatment fluid is placed in the enclosed space 20. The wand tip 14 and front seal 16 are then put back in place, a pad 24 is placed in the pad chamber 15 in the wand tip 14, the vacuum is turned on and adjusted by occluding the wand tip 14 against a skin surface and the flow rate on the wand 10 is set. The wand 10 is then placed against the skin surface to be treated with the distal end partially occluded so that air is pulled into the wand tip 14, through the central opening in the pad 24 and up the vacuum tube 22. This also draws fluid from the enclosed space 20 into the pad 24. The wand 10 is then used in a normal manner, such as shown in applicants prior U.S. Pat. Nos. 6,241,739 and 6,500,135, incorporated herein by reference, to perform skin abrasion accompanied by use of the treatment fluid 42.

Using a closed cell rubber foam as a skin substitute various flow settings and vacuum levels, as listed below in Table 1, were tested. The wand was passed over the foam in 4-inch long strokes for twenty-five passes which is equivalent to a facial treatment over a typical 5-15 minute time span. The "Flow" listed below is the amount of treatment fluid delivered per the 5-15 minute procedure.

TABLE 1

Flow Rate Testing of the Fluid Delivery Wand.

| Test Fluid[1] | Wand Setting | Vacuum Setting In-hg | Flow (CC) | Waste[2] (CC) |
|---|---|---|---|---|
| LRS100 | 1 | 5 | 0.25 | 0.1 |
| LRS100 | 2 | 5 | 0.3 | 0.1 |
| LRS100 | 3 | 5 | 0.5 | 0.1 |
| LRS100 | 1 | 8 | 0.75 | 0.1 |
| LRS100 | 2 | 8 | 1 | 0.1 |
| LRS100 | 3 | 8 | 1.5 | 0.1 |
| Mineral Oil | 1 | 5 | 2 | 1 |
| Mineral Oil | 2 | 5 | 4 | 1 |
| Mineral Oil | 3 | 5 | 5 | 1 |

[1]LRS100 is a moderate viscosity skin treatment product comprising plant derived lipids (sphingolipids), anti-inflammatory agents, nutritional and moisturizing agents in emollient base available from Custom Dermaceuticals, Inc., Randolph, NJ. Mineral Oil viscosity is slightly greater than water.
[2]The waste liquids constituters the fluid that did not reach the filter and was accumulated along the walls of the tubular canister 12.

Other examples of treatment fluids include C-serum and Even Skintone Serum available from Ultraceuticals Pty Ltd of Gladesville NSW, Australia. However, these treatment fluids are merely representative of numerous other skin treatment fluids and lotions known to practitioners in the field may be used in the liquid delivery wand described herein.

We claim:

1. A device for performing fluid assisted skin dermabrasion comprising a:
   a fluid storage chamber, said fluid storage chamber having a removable front and rear seal, each with a centrally located longitudinal hole there through, a vacuum tube positioned in the fluid storage chamber, through the centrally located holes and extending through a distal end of the front seal and a proximally end of the rear seal respectively in a substantially fluid tight manner, said front seal having a first flow channel extending longitudinally along an inner surface adjacent to an outer surface of the vacuum tube,
   a wand tip with a centrally located hole extending longitudinally there through removably positioned in an opening in the distal end of the front seal with the vacuum tube extending through the wand tip central hole in a substantially fluid tight manner, said wand tip having a second flow channel extending longitudinally along an inner surface adjacent to the outer surface of the vacuum tube, the wand also rotationally positioned in the front seal so that the first and second flow channels, in a first orientation, can be aligned to form a continuous flow channel.

2. The device of claim 1 wherein longitudinal alignment of the first flow channel and the second flow channel configures the device for maximum flow of fluid from the fluid storage chamber to a pad chamber on the distal end of the wand tip.

3. The device of claim 1 wherein rotation of the wand tip in the front seal orients the first flow channel and the second flow channel out of alignment and a 90° rotation of the wand tip from aligned to form a continuous flow channel configures the device for minimum flow of fluid from the fluid storage chamber to a pad chamber on the distal end of the wand tip.

4. The device of claim 3 wherein the vacuum tube has a spiral groove on the outer surface thereof along the length positioned in the centrally located longitudinal holes in the front seal; and wand tip, said spiral groove providing a flow channel for fluid flow from the fluid storage chamber to the pad chamber on the distal end of the wand tip, said spiral groove providing fluid flow when the front seal and wand tip are oriented for minimum flow.

\* \* \* \* \*